United States Patent
Kawai

(10) Patent No.: US 9,134,268 B2
(45) Date of Patent: Sep. 15, 2015

(54) MANUFACTURING METHOD FOR OXYGEN SENSOR

(75) Inventor: Masashi Kawai, Miyoshi (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 0 days.

(21) Appl. No.: 14/127,033

(22) PCT Filed: Jun. 13, 2012

(86) PCT No.: PCT/IB2012/001258
§ 371 (c)(1),
(2), (4) Date: Dec. 17, 2013

(87) PCT Pub. No.: WO2012/176063
PCT Pub. Date: Dec. 27, 2012

(65) Prior Publication Data
US 2014/0134329 A1 May 15, 2014

(30) Foreign Application Priority Data
Jun. 20, 2011 (JP) .................................. 2011-136584

(51) Int. Cl.
*B05D 5/12* (2006.01)
*G01N 27/407* (2006.01)
*C23C 16/56* (2006.01)
*B05D 3/04* (2006.01)
*C23C 14/58* (2006.01)

(52) U.S. Cl.
CPC .......... *G01N 27/407* (2013.01); *G01N 27/4075* (2013.01); *B05D 3/04* (2013.01); *C23C 14/58* (2013.01); *C23C 14/5853* (2013.01); *C23C 16/56* (2013.01)

(58) Field of Classification Search
USPC ................. 427/125, 377, 383.1, 383.3, 383.5
See application file for complete search history.

(56) References Cited

U.S. PATENT DOCUMENTS

| | | | |
|---|---|---|---|
| 4,253,931 A | 3/1981 | Gold et al. | |
| 4,477,487 A * | 10/1984 | Kojima et al. | 427/123 |
| 4,655,892 A * | 4/1987 | Satta et al. | 204/192.15 |
| 4,940,528 A | 7/1990 | Oki et al. | |
| 6,025,205 A | 2/2000 | Park et al. | |
| 6,071,554 A * | 6/2000 | Isomura et al. | 427/125 |
| 2002/0121441 A1 * | 9/2002 | Reidmeyer et al. | 204/424 |

FOREIGN PATENT DOCUMENTS

| | | | |
|---|---|---|---|
| GB | 2 162 324 A | | 1/1986 |
| JP | 57-207856 A | | 12/1982 |
| JP | 61120055 | * | 6/1986 |
| JP | 05-099895 A | | 4/1993 |
| JP | 08-020404 B2 | | 3/1996 |
| JP | 3094382 B2 | | 8/2000 |
| JP | 2000-277818 A | | 10/2000 |

OTHER PUBLICATIONS

International Search Report for corresponding International Patent Application No. PCT/IB2012/001258 mailed Sep. 25, 2012.

* cited by examiner

*Primary Examiner* — Brian K Talbot
(74) *Attorney, Agent, or Firm* — Sughrue Mion, PLLC

(57) ABSTRACT

A manufacturing method for an oxygen sensor that includes an oxygen sensor element includes: coating both surfaces of a solid electrolyte element of the oxygen sensor element with Pt films as a pair of electrodes; and heating at least one of the coated Pt films, coated on a side exposed to measured gas, in a gas atmosphere having a higher oxygen gas concentration than atmospheric gas to align a crystal orientation of the at least one of the Pt films with a (001) plane.

5 Claims, 4 Drawing Sheets

MANUFACTURING METHOD FOR OXYGEN SENSOR

BACKGROUND OF THE INVENTION

1. Field of the Invention

The invention relates to a manufacturing method for an oxygen sensor that has an oxygen sensor element coated with a Pt film and, more particularly, to a manufacturing method for an oxygen sensor having excellent detection accuracy.

2. Description of Related Art

In an existing art, an oxygen sensor (O2 sensor) has an oxygen sensor element, and the oxygen sensor element is accommodated in a housing. For example, in the case of a closed-end cylindrical (cup-shaped) oxygen sensor element, there is known an oxygen sensor element that includes a cup-shaped solid electrolyte element having oxygen ion conductivity, an inner electrode that is provided on the inner surface of the solid electrolyte element and an outer electrode that is provided on the outer surface of the solid electrolyte element.

In such an oxygen sensor element, the inner electrode is brought into contact with the atmosphere to serve as a reference electrode and the outer electrode is brought into contact with a measured gas to serve as a measuring electrode. By so doing, the concentration of oxygen in exhaust gas from an internal combustion engine is measured.

In recent years, in order to improve the performance of an oxygen sensor element, various studies have been made on the outer electrode. For example, in order to improve low-temperature operability and gas responsiveness, an oxygen sensor element of which the mean particle diameter of electrode material crystals of an outer electrode and the thickness of the outer electrode are improved is disclosed (for example, see Japanese Patent Publication No. 8-20404). Here, a solid electrolyte element that constitutes the oxygen sensor element is made of stabilized zirconia, and the surface of the solid electrolyte element is coated with a platinum (Pt) film as an electrode material.

A coating method for such a Pt film may be generally, for example, a coating method using PVD, CVD, or the like. For example, there are suggested a method in which a Pt film is coated by sputtering in an atmosphere of nitrogen (for example, see Japanese Patent No. 3094382) and a method in which the (100) plane of an Si substrate is subjected to etching to roughen the surface, an yttria-stabilized zirconia layer is laminated on the surface and the yttria-stabilized zirconia layer is coated with a Pt film in an atmosphere of Ar gas (for example, see Japanese Patent Application Publication No. 2000-277818 (JP 2000-277818 A).

Incidentally, in air-fuel ratio control over an internal combustion engine of an automobile, the air-fuel ratio is adjusted on the basis of an output voltage of an oxygen sensor element, and the oxygen sensor element has such a characteristic that the output voltage steeply varies around a stoichiometric air-fuel ratio.

Therefore, by adjusting the air-fuel ratio (executing feedback control) on the basis of the output voltage of the oxygen sensor element using the characteristic that the output voltage steeply varies, the internal combustion engine is allowed to operate at substantially an ideal air-fuel ratio. Note that, generally, in an oxygen sensor element, (air-fuel ratio at the time when the output voltage steeply varies)/(stoichiometric air-fuel ratio) is denoted by a control value $\lambda$ and then air-fuel ratio control is executed on the basis of the control value $\lambda$.

The output voltage of the oxygen sensor element desirably varies quickly in response to a change between rich/lean atmospheres irrespective of the concentration of gas; however, the above described existing oxygen sensor elements do not sufficiently have such trackability (responsiveness).

The reason will be described below. As described above, the oxygen sensor indicates a change of a measured gas atmosphere as an output value with reference to the amount of oxygen in the atmosphere. Therefore, the trackability of the output voltage depends on the ability to quickly change an oxygen condition of a solid electrolyte interface via the measured gas-side electrode. Here, in a high-concentration gas environment, an oxygen condition quickly varies, so the above described responsiveness does not significantly matter. However, in an environment of which the concentration of a measured gas is low, the response time of the oxygen sensor element tends to extend with a variation in the oxygen condition. Therefore, there may temporarily occur a deviation between the oxygen concentration of the measured gas and the output voltage of the oxygen sensor. Thus, controllability of air-fuel ratio control deteriorates and, as a result, emissions may deteriorate.

On the other hand, in the above described oxygen sensor elements, the control value $\lambda$ after usage for a certain period may vary from the control value $\lambda$ immediately after production. As the control value $\lambda$ varies, it may lead to a situation that the initially set exhaust gas purification performance of a catalyst device becomes insufficient thereafter.

The reason will be described below. In comparison with an initially set condition of an oxygen sensor, the condition of the oxygen sensor that has been endured in a vehicle is such that the forms of the electrode and electrode interface that are gas reaction portions vary because they are subjected to various thermal history and exhaust gas environments. As a result, the responsiveness, amount, diffusibility, and the like, of gas fluctuate, so the output of the oxygen sensor becomes unstable (the control value $\lambda$ varies).

SUMMARY OF THE INVENTION

The invention provides a manufacturing method that is able to manufacture an oxygen sensor having excellent responsiveness and less temporal variation in output in usage.

The inventors diligently studied and obtained the following new findings. A Pt film coated on a surface of a sensor element of an oxygen sensor for exhaust gas is subjected to predetermined heat treatment to thereby align the crystal orientation in a constant direction. By so doing, the dissociation and adsorption ability of the sensor element for lean gas (low-concentration gas), such as O2 and NOx, may be enhanced (detection sensitivity may be enhanced). Thus, it is possible to improve emissions and fuel economy of an internal combustion engine.

An aspect of the invention relates to a manufacturing method for an oxygen sensor that includes an oxygen sensor element. The manufacturing method includes: coating both surfaces of a solid electrolyte element of the oxygen sensor element with Pt films as a pair of electrodes; and heating at least one of the coated Pt films, coated on a side exposed to measured gas, in a gas atmosphere having a higher oxygen gas concentration than atmospheric gas to align a crystal orientation of the at least one of the Pt films with a (001) plane.

Here, in the aspect of the invention, the phrase "align a crystal orientation of the at least one of the Pt films with a (001) plane" means that the crystal orientation is aligned with the (001) plane such that the crystal orientation of Pt present at least on the surface of the at least one of the Pt films is oriented in the (001) plane.

According to the aspect of the invention, by heating the Pt film under the above described heating condition, the crystal orientation of the electrode (Pt film) on the side exposed to the measured gas varies, and the electrode has an electrode structure having an increased rate of the Pt film at the (001) plane, which is advantageous in dissociation and adsorption of oxygen. By so doing, dissociation and adsorption ability of oxygen in the electrode improves in comparison with before, so the oxygen sensor that includes the oxygen sensor element is able to improve responsiveness (sensitivity) against extremely low-concentration lean gas in exhaust gas.

As a result, it is possible to achieve stable engine system control that early feeds back a variation in the atmosphere of exhaust gas. By so doing, in comparison with the existing oxygen sensor, it is possible to achieve low fuel consumption and low emissions of the internal combustion engine.

Furthermore, the structure of the electrode and the structure of the interface between the electrode and the solid electrolyte element are annealed by the heat treatment, so the constitution is stabilized. As a result, the electrodes are stabilized in an active state (the electrodes are hard to vary in condition at sensor usage temperatures), so the temporal variation of the sensor characteristic is reduced as compared with the existing one.

In the above aspect, when the crystal orientation is aligned, the at least one of the Pt films may be heated at a heating temperature of 1000° C. to 1300° C. for at least a heating time of an hour or longer. According to this aspect, when the crystal orientation is aligned in the above heating condition, it is possible to further increase the rate of the Pt film at the (001) plane, which serves as the electrode.

That is, when the heating temperature is lower than 1000° C. or when the heating time is shorter than an hour, the rate at which the above described Pt film is aligned with the (001) plane is not sufficient; whereas, when the heating temperature exceeds 1300° C., degradation of the electrode may be accelerated because of the progress of agglomeration of Pt.

Here, when the crystal orientation is aligned, the gas atmosphere having a higher oxygen gas concentration than atmospheric gas may be a gas atmosphere having a higher oxygen partial pressure than atmospheric gas, a gas atmosphere in which ozone gas having a high oxidizing property is present together with atmospheric gas, or the like. As long as the crystal orientation of the Pt film may be aligned at the time of the above heat treatment, the gas atmosphere is not limited.

In the above aspect, when the crystal orientation is aligned, the oxygen gas concentration may be 50 percent by volume or above. According to this aspect, the crystal orientation varies for the heating time of about an hour, and the electrode structure having an increased rate of the Pt film at the (001) plane may be obtained.

In addition, a method of coating the Pt film on the surface of the solid electrolyte element may be a method of coating a pasty Pt film, a method of coating the Pt film using PVD or CVD, a method of coating the Pt film by plating, or the like. As long as the Pt film may be coated on the surface of the solid electrolyte element, the method is not specifically limited.

In the above aspect, the at least one of the Pt films may be coated by electroless platinum plating. According to this aspect, for example, when the shape of the solid electrolyte element is a complex shape, such as a closed-end cylindrical shape, the Pt film may be easily coated on the inner surface. Furthermore, the crystal orientation of crystal grains of the Pt film formed by electroless platinum plating presumably grows randomly or in the [111] direction, and, even when the Pt film is coated by such a method, the crystal orientation may be easily aligned with the (001) plane that is advantageous in dissociation and adsorption of oxygen through the above described heat treatment.

According to the above aspect, it is possible to manufacture the oxygen sensor that has excellent responsiveness and that has a small temporal variation in output in usage.

BRIEF DESCRIPTION OF THE DRAWINGS

Features, advantages, and technical and industrial significance of exemplary embodiments of the invention will be described below with reference to the accompanying drawings, in which like numerals denote like elements, and wherein:

FIG. 2A and FIG. 2B are views that show the results of EBSD analysis of electrodes (Pt films) formed on oxygen sensor elements according to a first example and a first comparative example, in which FIG. 2A is an inverse pole figure of EBSD analysis of the electrode (Pt film) formed on the oxygen sensor element of the first example and FIG. 2B is an inverse pole figure of EBSD analysis of the electrode (Pt film) formed on the oxygen sensor element of the first comparative example;

DETAILED DESCRIPTION OF EMBODIMENTS

Hereinafter, a manufacturing method for an oxygen sensor according to an embodiment of the invention will be described.

Figure 1:
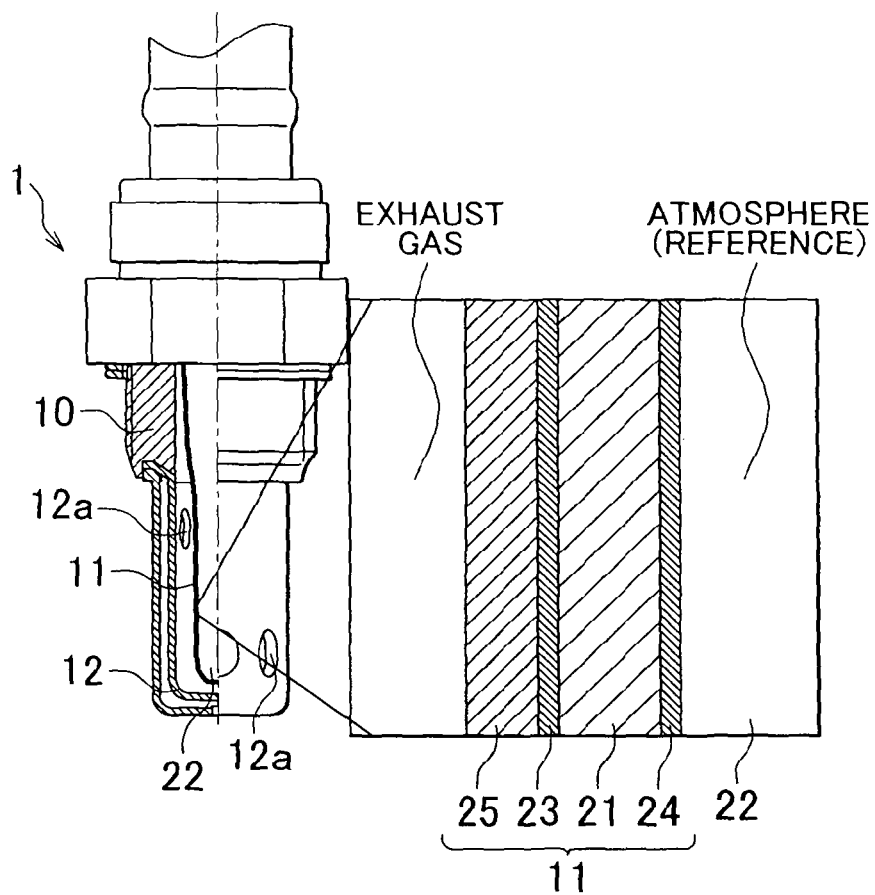
FIG. 1 is a schematic cross-sectional view of an oxygen sensor and an oxygen sensor element included in the oxygen sensor according to an embodiment.

FIG. 1 is a schematic cross-sectional view of an oxygen sensor and an oxygen sensor element included in the oxygen sensor according to the present embodiment. As shown in FIG. 1, the oxygen sensor 1 according to the present embodiment is installed in an exhaust pipe of an internal combustion engine. The oxygen sensor 1 detects the concentration of oxygen or the concentration of unburned fuel in exhaust gas of the internal combustion engine, and then detects the air-fuel ratio in a combustion chamber of the internal combustion engine on the basis of the concentration of oxygen or the concentration of unburned fuel.

Specifically, the oxygen sensor 1 includes an oxygen sensor element 11, and the oxygen sensor element 11 is fixedly inserted in a housing 10. The distal end side of the oxygen sensor element 11 is protected by a double-structure measured gas cover 12. In addition, the measured gas cover 12 has an introducing port 12a that introduces measured gas (exhaust gas). By so doing, measured gas may be introduced to an inner electrode 24 that is arranged inside the measured gas cover 12 (described later).

The oxygen sensor element 11, for example, has a closed-end cylindrical solid electrolyte element 21 and a pair of electrodes 23 and 24 on both surfaces of the solid electrolyte element 21. When the oxygen sensor element 11 is attached to the housing 10 of the oxygen sensor 1, the electrodes of the oxygen sensor element 11 are located inside the measured gas cover 12.

More specifically, the outer surface of the solid electrolyte element 21 is coated with a Pt film that serves as the outer electrode 23, and a porous protection layer (or a diffused resistor layer) 25 is formed to cover the outer electrode 23. On the other hand, an atmospheric chamber 22 that introduces the atmosphere is formed on the inner surface side of the oxygen sensor element 11, and the inner surface of the solid electrolyte element 21 is coated with the inner electrode 24. In this way, the oxygen sensor element 11 is configured such that the outer electrode (one of the electrodes) 23 of the above described pair of electrodes 23 and 24 is exposed to measured gas and the inner electrode (the other one of the electrodes) 24 is exposed to reference gas (atmosphere).

Note that, here, the oxygen sensor element may be generally known yttria-stabilized zirconia (YSZ); however, the oxygen sensor element is not specifically limited as long as the material has ion conductivity and excellent thermal resistance.

The thus obtained oxygen sensor 1 is attached to the exhaust pipe of the internal combustion engine. At this time, the inner electrode 24 exposed to the atmosphere serves as a reference electrode, and the outer electrode 23 exposed to exhaust gas serves as a measuring electrode. A concentration cell is formed between the outer electrode 23 and the inner electrode 24 because of the difference in oxygen concentration. By measuring a difference in potential (voltage) between the electrodes, the oxygen concentration may be measured.

For example, when exhaust gas changes into rich gas, the difference in oxygen concentration between exhaust gas and atmospheric gas increases, so the output voltage of the oxygen sensor increases. On the other hand, when exhaust gas changes into lean gas, the difference in oxygen concentration between exhaust gas and atmospheric gas reduces, so the output voltage of the oxygen sensor reduces.

The above described oxygen sensor element 11 is manufactured as follows. Initially, the closed-end solid electrolyte element 21 that has the atmospheric chamber 22 inside and that is made of yttria-stabilized zirconia (YSZ) is molded.

Subsequently, the outer surface of the solid electrolyte element 21 is coated with a PT film as the outer electrode 23 by electroless platinum plating. Specifically, a platinum solution is used as a plating solution. The platinum solution is heated to a predetermined liquid temperature. An additive, such as a reductant, is put into the platinum solution. Then the solid electrolyte element and/or a jig that holds the solid electrolyte element are oscillated at a predetermined oscillation speed. By so doing, platinum is precipitated on the outer surface of the solid electrolyte element. After that, the solid electrolyte element plated with platinum is washed by water and dried. Thus, the outer electrode (Pt film) 23 having a thickness of 1 to 2 μm is formed.

Subsequently, the outer electrode 23 is heated at a predetermined heating temperature (firing temperature) (1000 to 1200° C.) for an hour in the atmosphere to fire the platinum of the outer electrode 23. Subsequently, in order to protect the outer electrode 23, a porous protection layer made of spinel (MgAl2O4) is formed by plasma spraying. Furthermore, the inner electrode 24 is formed on the inner surface of the solid electrolyte element (element) by electroless platinum plating.

Finally, the oxygen sensor element 11 on which the outer electrode 23 and the inner electrode 24 are formed is heated at a predetermined heating temperature (1100 to 1300° C.) higher than the above described firing temperature of the outer electrode 23 for an hour or longer in a gas atmosphere having an oxygen gas concentration higher than atmospheric gas (desirably, in an atmosphere having an oxygen concentration of 50 percent by volume or above or an atmosphere that contains ozone gas) (the Pt film is aged). By so doing, at least the crystal orientation of the Pt film of the outer electrode 23 is aligned with the (001) plane.

The thus configured oxygen sensor element 11 is assembled into the housing 10 as shown in FIG. 1, and the measured gas cover 12 is attached. Thus, the oxygen sensor 1 may be obtained.

In this way, usually, in formation of a film on polycrystalline ceramics, such as yttria-stabilized zirconia, the crystal orientation of crystal grains of the Pt film is estimated to grow randomly or in the [111] direction. However, through high-temperature heat treatment in a gas atmosphere having an oxygen gas concentration higher than atmospheric gas, the crystal orientation varies, and the electrode structure has an increased rate of the Pt film at the (001) plane, which is advantageous in dissociation and adsorption of oxygen.

In addition, the Pt film formed by electroless platinum plating is formed of fine Pt particle assemblage, so the Pt film melts under the above described aging condition and then recrystallizes, so the crystal orientation of the Pt film is easily aligned with the (001) plane.

The thus obtained oxygen sensor has improved responsiveness (sensitivity) for extremely low-concentration lean gas in exhaust gas, so it is possible to achieve stable engine system control that early feeds back a variation in the atmosphere of exhaust gas. By so doing, in comparison with the existing oxygen sensor, it is possible to achieve low fuel consumption and low emissions of the internal combustion engine. In addition, the above described method leads to a reduction in catalyst precious metal (Pt), so there is a significant merit in terms of cost. Through aging of the Pt film, the structure of the electrodes and the structure of the interface between each electrode and the solid electrolyte element are annealed, so the constitution is stabilized. As a result, the electrodes are stabilized in an active state (the electrodes are hard to vary in condition at sensor usage temperatures), so the temporal variation of the sensor characteristic is reduced as compared with the existing one.

EXAMPLES

First Example

The oxygen sensor was manufactured in the following manner. Specifically, the closed-end cylindrical solid electrolyte element made of yttria-stabilized zirconia (YSZ) (5 mol % yttrium oxide) was molded. Subsequently, the outer surface of the solid electrolyte element was coated with the outer electrode formed of the Pt film by electroless platinum plating. Specifically, a dinitrodiamine platinum solution (2 g/l) was used as a plating solution, and the plating solution was heated to 50° C. Subsequently, 80 percent by weight hydrazine solution as a reductant, 4 g/l stabilizer and ammonia water were put in the plating solution and prepared to within the range of pH11 to pH12. Then, the jig holding the solid electrolyte element was moved up and down at a predetermined oscillation speed (once/s). By so doing, platinum was precipitated on the outer surface of the solid electrolyte element. After that, the solid electrolyte element plated with platinum was washed by water and dried to form the outer electrode (Pt film) having a thickness of 2 μm. The outer electrode was heated by a heater at 1000° C. for an hour in the atmosphere to fire Pt.

Furthermore, the porous protection layer made of spinel (MgAl2O4) was formed on the outer electrode in a thickness of 200 μm by plasma spraying. Furthermore, the inner electrode was formed on the inner surface of the solid electrolyte element (element) by the same method (electroless platinum plating) as that of forming the outer electrode.

The oxygen sensor element on which the outer electrode and the inner electrode were formed was heated by a heater (aged) at a heating temperature of 1100° C. for an hour in a gas atmosphere that was formed by mixing 50 percent by volume oxygen concentration into nitrogen gas. By so doing, the crystal orientation of the Pt film was aligned with the (001) plane by utilizing recrystallization of Pt of the outer and inner electrodes. The thus obtained oxygen sensor element was assembled to the housing to thereby obtain the oxygen sensor.

Second Example

As in the case of the first example, the oxygen sensor was manufactured. The difference from the first example is that, when the crystal orientation of the Pt film was aligned with the (001) plane, the oxygen sensor element on which the outer electrode and the inner electrode were formed was heated in a gas atmosphere that was formed by mixing 30 percent by volume oxygen concentration into nitrogen gas.

First Comparative Example

As in the case of the first example, the oxygen sensor was manufactured. The difference from the first example is that the oxygen sensor element on which the outer electrode and the inner electrode were formed was not subjected to the above described aging.

Second Comparative Example

Figure 2A:
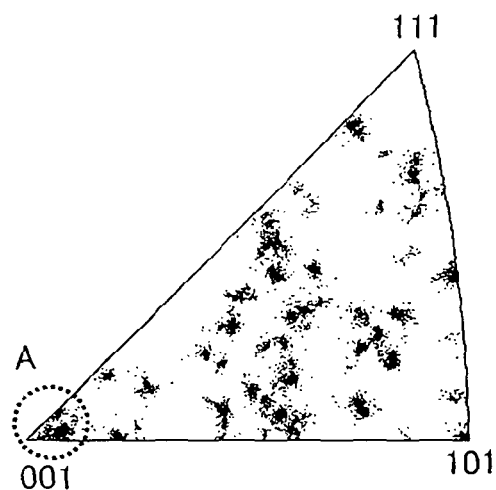
Figure 2B:
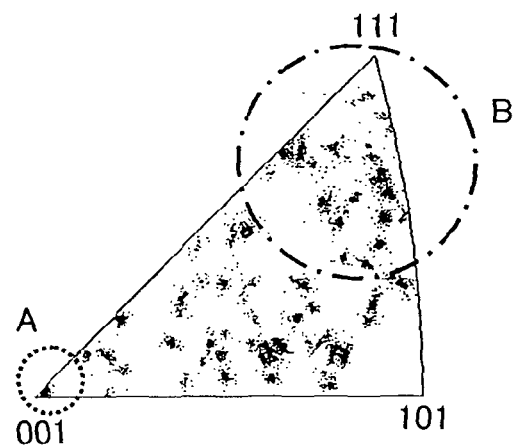

As in the case of the first example, the oxygen sensor was manufactured. The difference from the first example is that the oxygen sensor element on which the outer electrode and the inner electrode were formed was not subjected to the above described aging, and the manufacturing method is the same as that of the first comparative example.
Measurement of Orientation of Pt Film An electron beam was irradiated to the Pt films of the outer electrodes of the first and second examples and the Pt film of the outer electrode of the first comparative example by electron back scattering diffraction (EBSD) analysis, and the electron back scattering diffraction pattern generated at this time was captured. By so doing, the crystal orientation of the region in which the electron beam was irradiated was, measured. FIG. 2A and FIG. 2B are inverse pole figures in EBSD analysis of the Pt films according to the first example and the first comparative example.
Performance Evaluation 1

Figure 3:
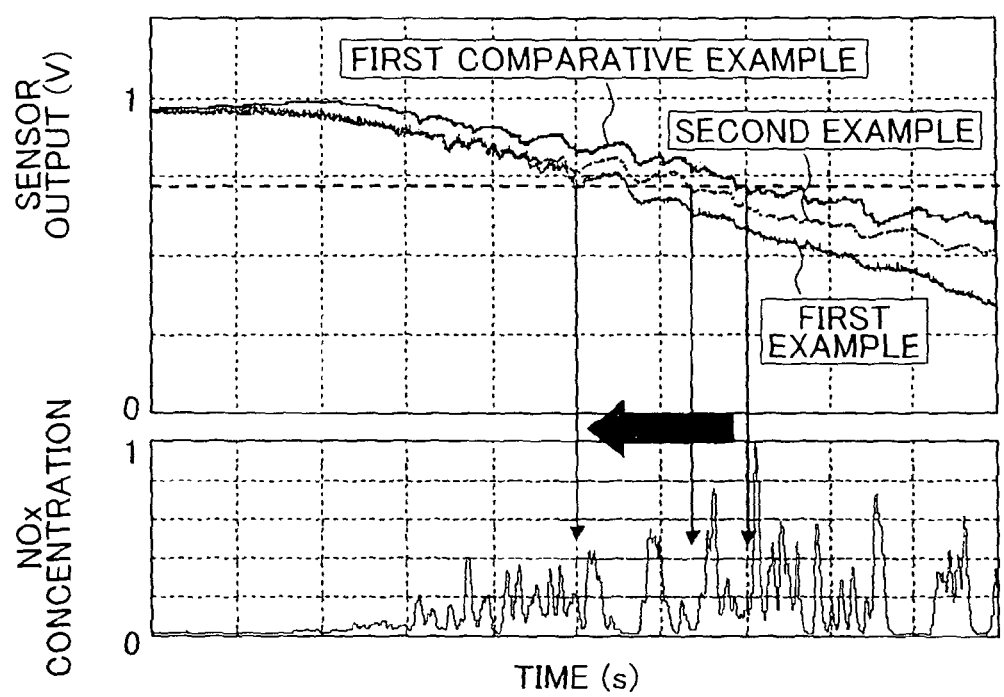
FIG. 3 is a graph that shows the correlations between a sensor output and an exhaust gas amount when oxygen sensors respectively according to the first example, a second example and the first comparative example are equipped for an actual device.

Each of the oxygen sensors according to the first and second examples and the first comparative example was mounted on the internal combustion engine (real machine), and then the real machine bench was gradually varied (swept) such that the gas environment varies from a rich air-fuel ratio to a lean air-fuel ratio near an air-fuel ratio of 14.6 (stoichiometric air-fuel ratio). By so doing, the NOx concentration and the output of each oxygen sensor at that time were measured. The results are shown in FIG. 3. Note that the NOx concentrations shown in FIG. 3 are values normalized by a predetermined concentration (ppm).

Performance Evaluation 2

Figure 4:
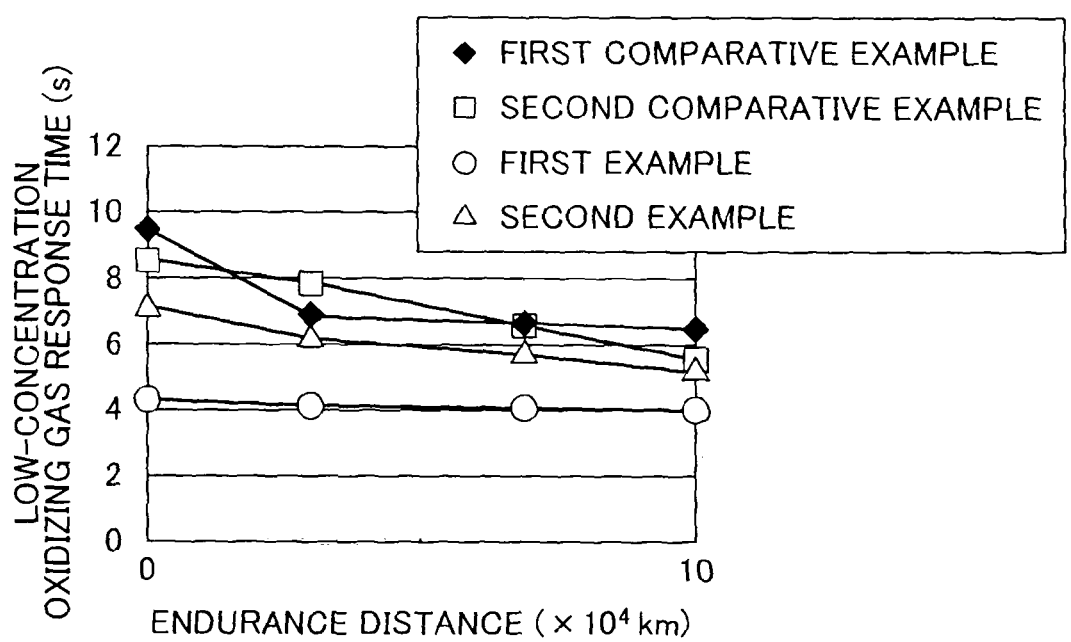
FIG. 4 is a graph that shows the correlations between an endurance distance of each of the oxygen sensors according to the first example, the second example, the first comparative example and a second comparative example and a low-concentration oxidizing gas response time.

Each of the oxygen sensors according to the first and second examples and the first and second comparative examples was mounted on the internal combustion engine (real machine), and the internal combustion engine was operated so as to correspond to travel distances (endurance distances) of 30000 km, 70000 km and 100000 km. Then, while each oxygen sensor was being exposed to rich gas having about several hundreds of ppm by a model gas characteristic evaluation device, the rich gas was changed to lean gas having several hundreds of ppm at the selected timing in a rectangular manner, and a period of time (response time) from the changed time to when the oxygen sensor indicates a predetermined sensor voltage was measured. The results are shown in FIG. 4.
Result 1

FIG. 2A shows the results of EBSD analysis of the electrode (Pt film) formed on the oxygen sensor element according to the first example. FIG. 2B shows the results of EBSD analysis of the electrode (Pt film) formed on the oxygen sensor element according to the first comparative example. As shown at portion A in FIG. 2A and FIG. 2B, the Pt films of the oxygen sensors according to the first and second examples each have a higher rate at the (001) plane than that of the first comparative example. In addition, the Pt film of the oxygen sensor according to the first comparative example has a higher rate at the (111) plane than the Pt film according to the first embodiment as shown at portion B in FIG. 2B. In addition, the Pt film according to the first example has a higher rate at the (001) plane than that of the second example.
Result 2

As shown in FIG. 3, the responsiveness of the oxygen sensors for a variation in NOx is higher in order of the first example, the second example and the first comparative example.
Result 3

As shown in FIG. 4, the oxygen sensors according to the first and second examples have smaller fluctuations in sensor output for an endurance distance than the oxygen sensors according to the first and second comparative examples. Furthermore, the oxygen sensor according to the first example has a stable sensor output irrespective of an endurance distance. In addition, the oxygen sensors according to the first and second comparative examples have large variations for an endurance distance although they were manufactured by the same manufacturing method.
Consideration 1

A metal, such as Pt, having a crystal structure of f.c.c. is estimated to have a low surface energy at the (111) plane and grows in the [111] direction. Thus, from the results 1 and 2, it may be assumed that, as in the case of the electrode of the oxygen sensor according to the first comparative example, Pt particles originally had grown in the [111] direction or randomly; however, as in the case of the first and second examples, the crystal orientation of Pt particles exposed to oxygen gas varied so as to increase the rate of the Pt film at the (001) plane, which is advantageous in dissociation and adsorption of oxygen in terms of energy, to thereby form the electrode structure shown by the inverse pole figure in FIG. 2A.

Furthermore, through high-temperature heat treatment in an atmosphere having a higher oxygen concentration (containing 50 percent by volume of oxygen gas) as in the case of the first example as compared with the second example, the rate of the Pt film at the (001) plane was increased. Thus, it is possible to increase the rate of the Pt film at the (001) plane as in the case of the first example by setting oxygen gas so as to be higher than or equal to 50 percent by volume. Note that ozone gas is decomposed to oxygen gas at the heating temperature at the time of aging the Pt film, so it is presumable that, even when, for example, ozone is introduced before aging so as to obtain an oxygen gas concentration higher than that of atmospheric gas at the time of decomposition of ozone gas, the results as in the case of the first and second examples are obtained.

Consideration 2

Furthermore, from the result 3, it may be assumed as follows. In the oxygen sensor with no aging according to the first comparative example, the electrode condition is not sufficiently activated against oxygen in a usage environment. On the other hand, in the oxygen sensors according to the first and second examples, the structure of the electrodes and the structure of the interface between each electrode and the solid electrolyte are annealed by aging, and the constitution is stabilized, so the condition is hard to vary at sensor usage temperatures. In addition, in the case of the second example, the heating time in aging was an hour; instead, it is presumable that the characteristic as in the case of the first example may be obtained with a longer heating time.

The embodiment of the invention is described in detail above; however, specific configurations are not limited to the embodiment and the examples. Even when there, are design changes without departing from the scope of the invention, those may be included in the aspect of the invention.

In the present embodiment, the outer electrode and the inner electrode each are formed of the Pt film by electroless plating; however, as long as the outer electrode and the inner electrode may be formed, the surface of the solid electrolyte element may be coated with the Pt film that serves as the electrode by sputtering, ion plating, plasma CVD, or the like, or may be coated with the Pt film that serves as the electrode using a platinum paste.

The invention claimed is:

1. A manufacturing method for an oxygen sensor that includes an oxygen sensor element, comprising:
   coating both surfaces of a solid electrolyte element of the oxygen sensor element with Pt films as a pair of electrodes; and
   heating at least one of the coated Pt films, coated on a side exposed to measured gas, in a gas atmosphere having a higher oxygen gas concentration than atmospheric gas to align a crystal orientation of the at least one of the Pt films with a (001) plane,
   wherein, when the crystal orientation is aligned, the oxygen gas concentration is 50 percent by volume or above and the at least one of the Pt films is heated at a heating temperature of 1000° C. to 1300° C., and
   the at least one of the Pt films is coated by electroless platinum plating.

2. The manufacturing method according to claim 1, wherein, when the crystal orientation is aligned, the at least one of the Pt films is heated at a heating temperature of 1000° C. to 1300° C. for at least a heating time of an hour or longer.

3. The manufacturing method according to claims 1 or 2, wherein the gas atmosphere having a higher oxygen gas concentration than atmospheric gas is any one of a gas atmosphere having a higher oxygen partial pressure than atmospheric gas and a gas atmosphere in which ozone gas is present together with atmospheric gas.

4. The manufacturing method according to claims 1 or 2, wherein both Pt films are coated by electroless platinum plating.

5. The manufacturing method according to claim 3, wherein both Pt films are coated by electroless platinum plating.

* * * * *